(12) United States Patent
Watanabe et al.

(10) Patent No.: US 8,298,486 B2
(45) Date of Patent: Oct. 30, 2012

(54) PIEZOELECTRIC RESONATOR AND SENSING SENSOR

(75) Inventors: Shigenori Watanabe, Sayama (JP); Takeru Mutoh, Sayama (JP); Mitsuaki Koyama, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 0 days.

(21) Appl. No.: 12/736,805

(22) PCT Filed: Mar. 2, 2009

(86) PCT No.: PCT/JP2009/054363
§ 371 (c)(1),
(2), (4) Date: Nov. 10, 2010

(87) PCT Pub. No.: WO2009/142046
PCT Pub. Date: Nov. 26, 2009

(65) Prior Publication Data
US 2011/0064614 A1    Mar. 17, 2011

(30) Foreign Application Priority Data

May 21, 2008   (JP) ................................ 2008-133659
Jun. 20, 2008  (JP) ................................ 2008-162266

(51) Int. Cl.
*G01N 15/06*    (2006.01)
*G01N 33/00*    (2006.01)
*G01N 33/48*    (2006.01)

(52) U.S. Cl. ..... 422/82.01; 422/50; 422/68.1; 422/82.02

(58) Field of Classification Search .................... 422/50, 422/68.1, 82.01, 82.02, 83
See application file for complete search history.

(56) References Cited

U.S. PATENT DOCUMENTS

| 5,744,902 | A  | * | 4/1998  | Vig ................................ 310/360 |
| 6,114,801 | A  | * | 9/2000  | Tanaka et al. ................... 310/365 |
| 6,196,052 | B1 | * | 3/2001  | May et al. ...................... 73/24.06 |
| 6,295,861 | B1 | * | 10/2001 | Tom et al. ...................... 73/24.06 |
| 7,552,639 | B2 |   | 6/2009  | Wakamatsu et al. |
| 2008/0047331 | A1 |   | 2/2008  | Wakamatsu et al. |

FOREIGN PATENT DOCUMENTS

| JP | 7-190916      | 7/1995  |
| JP | 10-142134     | 5/1998  |
| JP | 2004-317493   | 11/2004 |
| JP | 2004-340766   | 12/2004 |
| JP | 2006-003144   | 1/2006  |
| JP | 2006-033195   | 2/2006  |
| WO | WO-2006/064951 | 6/2006 |

\* cited by examiner

*Primary Examiner* — Brian J Sines
(74) *Attorney, Agent, or Firm* — Jordan and Hamburg LLP

(57) ABSTRACT

Objects of the present invention is to provide a piezoelectric resonator having high frequency stability and a sensing sensor using the piezoelectric resonator.

In the present invention, a piezoelectric resonator 1 has: a first oscillation area 105 which is provided in a piezoelectric piece 100 and from which a first oscillation frequency is taken out; a second oscillation area which is provided in an area 105 different from the first oscillation area 106 via an elastic boundary area 107 and from which a second oscillation frequency is taken out; and excitation electrodes 101 to 103 provided on one surface side and another surface side of the oscillation areas 105, 106 across the piezoelectric piece 100, and a frequency difference between the first oscillation frequency and the second oscillation frequency is not less than 0.2% nor greater than 2.2% of these oscillation frequencies.

4 Claims, 15 Drawing Sheets

(a)

(b)

(a)

(b)

PIEZOELECTRIC RESONATOR AND SENSING SENSOR

TECHNICAL FIELD

The present invention relates to a piezoelectric resonator capable of having a good frequency-temperature characteristic and a sensing sensor sensing a substance to be sensed by using the piezoelectric resonator.

BACKGROUND ART

As an instrument for sensing a trace substance in a solution or gas, there has been known a sensing instrument which uses QCM (Quarts Crystal Microbalance) formed of a piezoelectric resonator, for example, a quartz-crystal resonator. A sensing instrument of this type senses a trace substance being a substance to be sensed by making the quartz-crystal resonator adsorb the trace substance and finding a change in its oscillation frequency (resonant frequency). The present applicant has developed such a sensing instrument and expects that in future in various fields, it will become possible to sense, for example, dioxin being an environmental contaminant, specific antigens in blood or serum, and the like on an extremely low concentration level, for example, down to a ppb to ppt level.

Since the oscillation frequency of the quartz-crystal resonator used in the sensing instrument changes depending on temperature, some measure has to be taken in an oscillator circuit utilizing the quartz-crystal resonator in order to obtain frequency stability to temperature. Regarding this, there has been proposed a quartz-crystal resonator of a so-called twin sensor type that does not require a large-scale instrument structure such as an OCXO (Oven Controlled Crystal Oscillator) conventionally used, and is as compact and light-weighted as a TCXO (Temperature Compensated Crystal Oscillator) yet has higher frequency stability than the TCXO (for example, patent document 1 and patent document 2).

FIG. 5 is a structure example of a quartz-crystal oscillator 10 mounted in the sensing instrument developed by the present applicant, and the quartz-crystal oscillator 10 includes: a quartz-crystal resonator 1 of a twin sensor type structured such that excitation electrodes 101 to 103 are provided on a quartz-crystal piece 100 having two different oscillation areas (a first is oscillation area 105 and a second oscillation area 106) elastically insulated by an elastic boundary layer 107 being an elastic boundary area; and a pair of Colpitts oscillator circuits 111, 112 connected in series to the oscillation areas 105, 106 in order to take out oscillation frequencies from the oscillation areas 105, 106. For example, the excitation electrodes 101 to 103 are different in mass or size or the oscillator circuits 111, 112 are different in load capacitance, which makes it possible to obtain frequency signals with different oscillation frequencies from the respective oscillation areas 105, 106.

An adsorption layer capable of adsorbing a substance to be sensed is provided on the excitation electrode 103 on one of the areas (for example, the second oscillation area 106) of the quartz-crystal piece 100 and is capable of adsorbing a trace substance, and a block layer not adsorbing the substance to be sensed is provided on the excitation electrode 101 on the other area (for example, the first oscillation area 105). When a sample solution is supplied to a front surface of the quartz-crystal piece 100 on which these adsorption layer and block layer are formed, the substance to be sensed is selectively bonded with the adsorption layer to change the oscillation frequency of the second oscillation area 106 side on which the adsorption layer is formed. Hereinafter, an output of the first oscillation area 105 side will be called a channel 1 and an output of the second oscillation area 106 side will be called a channel 2. By subtracting the oscillation frequency of the channel 1 side from the oscillation frequency of the channel 2 side which has been influenced by the adsorption of the substance to be sensed and comparing the results before and after the adsorption, it is possible to find a variation in the oscillation frequency that is ascribable to the adsorption of the substance to be sensed.

As described above, the oscillation frequency of the quartz-crystal resonator changes according to a change in an ambient temperature, and here the principle for giving the quartz-crystal resonator 1 of the twin sensor type frequency stability to the temperature change will be described. A frequency-temperature characteristic 7b shown in FIG. 18 shows how the oscillation frequency in the second oscillation area 106 in the state of not adsorbing the substance to be sensed changes in accordance with a temperature change. When the frequency-temperature characteristic 7b of the second oscillation area 106 presents such a change, a variation in the oscillation frequency shown by a frequency-temperature characteristic 7a of the first oscillation area 105 provided on the common quartz-crystal piece 100 is substantially the same as that shown by the frequency temperature characteristic 7b of the second oscillation area 106 side as shown in FIG. 18.

Therefore, even when the oscillation frequencies from the first oscillation area 105 and the second oscillation area 106 change due to the change in the ambient temperature, a difference between the oscillation frequencies (frequency difference) of the both channels is substantially constant and does not change. Therefore, by comparing the frequency differences before and after the adsorption of the substance to be sensed, it is possible to highly accurately find a variation in the oscillation frequency caused by the adsorption, from which the influence of the frequency-temperature characteristic is removed.

After conducting various studies with the intention of achieving the practical application of a sensing instrument having high stability to, for example, a temperature change by using the quartz-crystal resonator 1 of the twin sensor type described above, the present inventors have found out that the following problem arises when the frequency difference between the two channels is too small or too large. Specifically, it has been found out that, when the oscillation frequencies of the first oscillation area 105 and the second oscillation area 106 are set to close values to thereby make the frequency difference therebetween small, the frequency difference between a frequency-temperature characteristic 71a of the first frequency area and a frequency-temperature characteristic 71b of the second frequency area does not become constant and the frequency difference unstably changes in accordance with a change in the ambient temperature as shown in FIG. 19, for instance. A possible reason for this is that, when the frequency difference between the both channels is reduced by setting the oscillation frequencies of the first oscillation area 105 and the second oscillation area 105 to close values, the two oscillation areas 105, 106 come into a state of being elastically coupled even though the elastic boundary layer 107 is provided. Such unstable change in the frequency difference not only makes it difficult to accurately find a variation in the oscillation frequency caused by the adsorption of the substance to be sensed but also lowers a function for accurately finding the variation in the oscillation frequency caused by the adsorption of the substance to be sensed because due to the elastic coupling of the two oscillation areas 105, 106, a change in an oscillation state of the second oscillation area 106 side caused by the adsorption of the substance to be sensed also changes the oscillation frequency of the first oscillation area 105 side not sensing the substance to be sensed.

When the oscillation frequencies of the first oscillation area 105 and the second oscillation area 106 are set greatly different from each other and thus the frequency difference is made large, the frequency difference between the frequency-temperature characteristic 72a of the first oscillation area 105 and the frequency-temperature characteristic 72b of the second oscillation area 106 tends to gradually increase as shown in FIG. 20, for instance; therefore, in this case, the method of canceling the influence of the frequency-temperature characteristic by finding the difference between the oscillation frequencies of the both channels cannot be employed either. The patent document 1 and the patent document 2 mentioned above do not find these problems that the quartz-crystal resonator of the twin sensor type has, and nor do they mention a solution to these problems.

PRIOR ART DOCUMENT

Patent Document 1

Japanese Patent Application Laid-open No. 2006-33195: claim 1, paragraph 0012 to paragraph 0014, paragraph 0018 to paragraph 0019, FIG. 1, FIG. 4

Patent Document 2

Japanese Patent Application Laid-open No. 2006-3144: paragraph 0014 to paragraph 0015, paragraph 0019, FIG. 2, FIG. 4

SUMMARY OF THE INVENTION

The present invention has been developed under the above circumstances and has an object to provide a piezoelectric resonator having high frequency stability and a sensing sensor using the piezoelectric resonator.

A piezoelectric resonator according to the present invention includes:

a first oscillation area which is provided in a piezoelectric piece and from which a first oscillation frequency is taken out under a predetermined reference temperature atmosphere;

a second oscillation area which is provided in an area, of the piezoelectric piece, different from the first oscillation area and from which a second oscillation frequency different from the first oscillation frequency is taken out under the reference temperature atmosphere;

an elastic boundary area provided in an area, of the piezoelectric piece, between the first oscillation area and the second oscillation area; and excitation electrodes provided on one surface side and another surface side of the piezoelectric piece in the first oscillation area and the second oscillation area, wherein a frequency difference between the first oscillation frequency and the second oscillation frequency is not less than 0.2% nor greater than 2.2% of the first and second oscillation frequencies.

The oscillation frequencies each are preferably not lower than 4.0 MHz nor higher than 200 MHz.

Further, the frequency difference is preferably adjusted by making values of at least one of the following (i) and (ii) different between the first oscillation area and the second oscillation area: (i) masses of the excitation electrodes provided on the one surface side and the other surface side across the piezoelectric piece in the first oscillation area and the second oscillation area; and (ii) thicknesses of the piezoelectric piece in the first oscillation area and the second oscillation area.

Next, a sensing sensor according to the present invention is a sensing sensor sensing a substance to be sensed in a sample solution based on an oscillation frequency of a piezoelectric resonator, the sensing sensor including:

a holder in which a hole portion is formed;

the piezoelectric resonator held by the holder, having excitation electrodes on one surface side and another surface side of a piezoelectric piece, and provided to cover the hole portion, with the excitation electrode on the other surface side facing an inside of the hole portion; and an adsorption layer provided on a front surface of the excitation electrode on the one surface side to adsorb the substance to be sensed, wherein one of the previously described piezoelectric resonators is used as the piezoelectric resonator, the adsorption layer is formed on the excitation electrode on the one surface side of one of the first oscillation area and the second oscillation area, and a frequency difference between the first oscillation frequency and the second oscillation frequency in an atmosphere where the substance to be sensed is sensed is not less than 0.2% nor greater than 2.2% of the first and second oscillation frequencies.

EFFECT OF THE INVENTION

According to the present invention, the difference between the oscillation frequencies of the two oscillation areas provided in the piezoelectric resonator of the twin sensor type is 0.2% to 2.2% of these oscillation frequencies. When the oscillation frequency difference falls within such a range, mutual interference of the oscillation frequencies due to elastic coupling of the two oscillation areas is small, which makes it possible to accurately take out the oscillation frequencies of the respective areas. Further, when the oscillation frequency difference falls within this range, since the two areas have the same frequency-temperature characteristic, it is possible to effectively cancel the influence of the frequency-temperature characteristics by taking a difference between these oscillation frequencies. As a result, in a case where, for example, the piezoelectric resonator is applied to a sensing sensor, highly reliable sensing results can be obtained.

MODE FOR CARRYING OUT THE INVENTION

Figure 1:
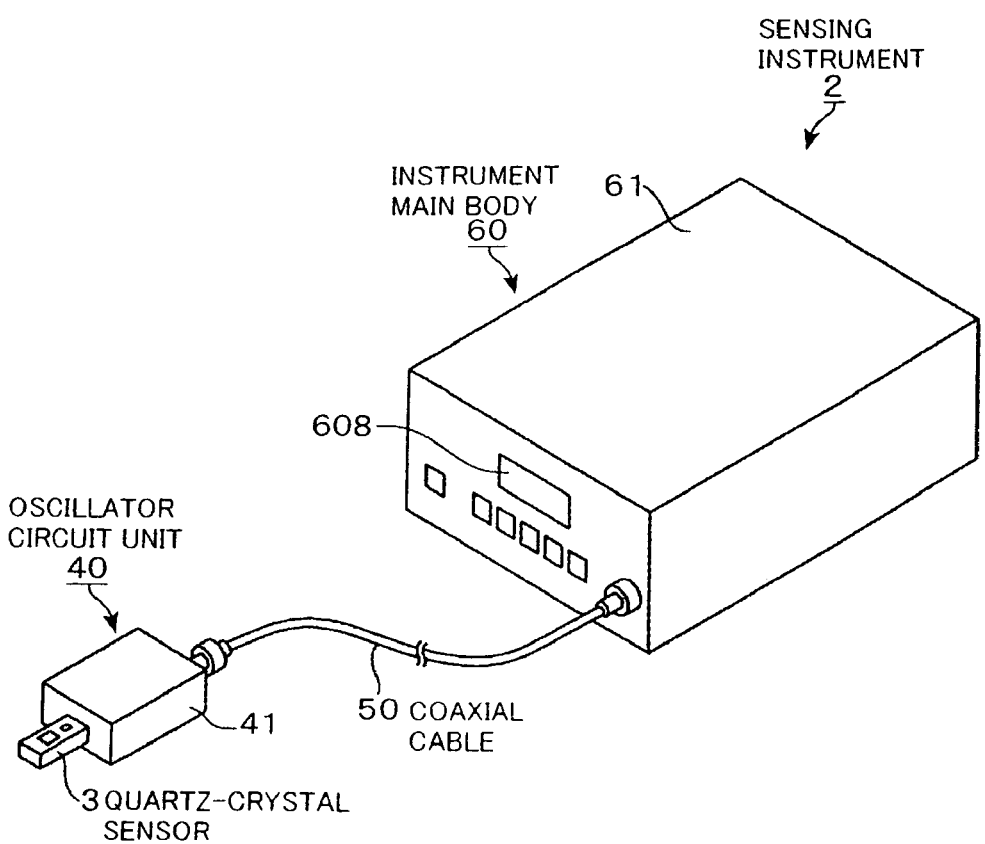
FIG. 1 is an external structure view of a sensing instrument according to an embodiment.

Hereinafter, as a sensing instrument 2 including a quartz-crystal resonator 1 according to this embodiment, a sensing instrument 2 having a function of sensing a specific antigen in blood or serum, for instance, will be described. As shown in an external structure view in FIG. 1, the sensing instrument 2 includes an oscillator circuit unit 40 and an instrument main body 60, and the oscillator circuit unit 40 is attachably/detachably connected to the instrument main body 60 by a cable, for example, a coaxial cable 50. A display part 608 provided on a front surface of a casing 61 of the instrument main body 60 plays a role of displaying measurement results of, for example, frequencies, variations in the frequencies, and so on and is formed by, for example, a LED display screen or a liquid crystal display screen.

Figure 2:
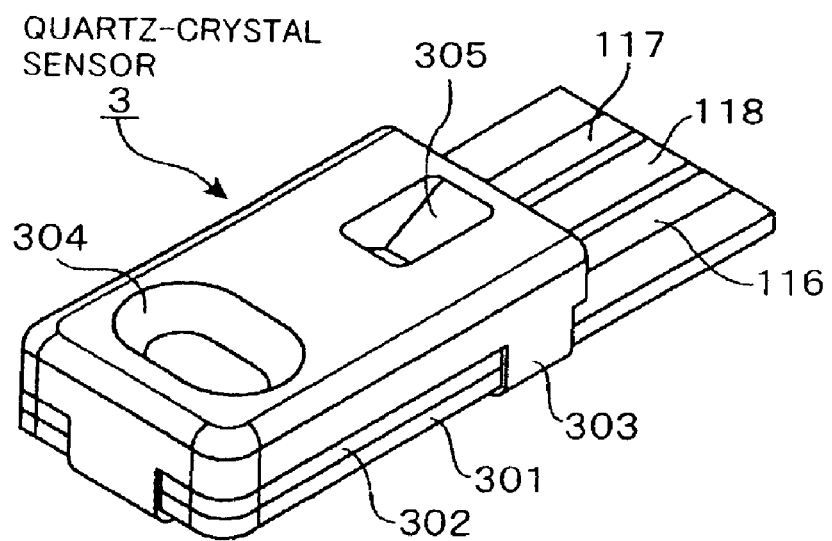
FIG. 2 is an external structure view of a quartz-crystal sensor connected to the sensing instrument.

A quartz-crystal sensor 3 being a sensing sensor whose external structure is shown in FIG. 2 is attachably/detachably connected to the oscillator circuit unit 40. The quartz-crystal sensor 3 is structured such that a rubber sheet 302 is stacked on a printed circuit board 301 whose one end is a connection terminal, the quartz-crystal resonator 1 which will be described later is disposed to cover a not-shown concave portion provided in the rubber sheet 302, and an upper cover case 303 is mounted from an upper side of the rubber sheet 302. With this structure, the concave portion on a lower surface side of the quartz-crystal resonator 1 becomes airtight space, so that a quartz-crystal sensor of a Languban type is formed. In the upper cover case 303, an injection port 304 for sample solution and a check port 305 for sample solution are formed, and when the sample solution is injected from the injection port 304, space on an upper surface side of the quartz-crystal resonator 1 can be filled with the sample solution. Here, the printed circuit board 301 and the rubber sheet 302 correspond to a holder of the present invention, and the concave portion provided in the rubber sheet 302 corresponds to a hole portion of the present invention.

As shown in perspective views seen from an upper side and a lower side in FIG. 3(a) and FIG. 3(b), for instance, the quartz-crystal resonator 1 is structured such that a groove portion serving as an elastic boundary layer 107 is formed in, for example, a front surface being one surface side of a quartz-crystal piece 100 in a circular shape, that is, in a surface in contact with the sample solution, to extend along a diameter direction, so that the front surface of the quartz-crystal piece 100 is divided into two semicircular areas by the elastic boundary layer 107. On substantially center portions of the respective semicircular areas, excitation electrodes 101, 103 in a circular shape made of, for example, gold are provided to be apart from each other with the aforesaid elastic boundary layer 107 therebetween, and these excitation electrodes 101, 103 are disposed to face each other in a direction perpendicular to the elastic boundary layer 107. As shown in FIG. 3(b), on a peripheral edge portion of a rear surface side being the other surface side of the quartz-crystal piece 100, two terminals 113, 114 apart from each other are provided so as to face each other in the same direction in which the excitation electrodes 101, 103 face each other, and the excitation electrodes 101, 103 are connected to the terminals 113, 114 respectively.

Further, on the rear surface side of the quartz-crystal piece 100, an excitation electrode 102 made of, for example, gold is formed in an area connecting surfaces (shown by the broken lines in FIG. 3(b)) where the excitation electrodes 101, 103 formed on the front surface side are projected to the rear surface. The excitation electrode 102 is connected to a terminal 115 disposed, for example, at a position which is on the peripheral edge portion of the rear surface of the quartz-crystal piece 100 and is a mid position between the aforesaid two terminals 113, 114. In the quartz-crystal piece 100 having the above-described structure, an area sandwiched by the excitation electrodes 101, 102 on one side provided on the front and rear surfaces corresponds to a first oscillation area 105, and an area sandwiched by the excitation electrodes 103, 102 on the other side corresponds to a second oscillation area 106. In this example, the elastic boundary layer 107 elastically insulating the two oscillation areas 105, 106 is the groove portion formed in one surface of the quartz-crystal piece 100, for instance, but it should be noted that a structure example of the elastic boundary layer 107 is not limited to this, and the aforesaid groove portion may be provided in the both surfaces of the quartz-crystal piece 100, or a conductive layer made of, for example, a metal film may be formed along the both surfaces of the quartz-crystal piece 100 to realize the insulation.

Figure 4:
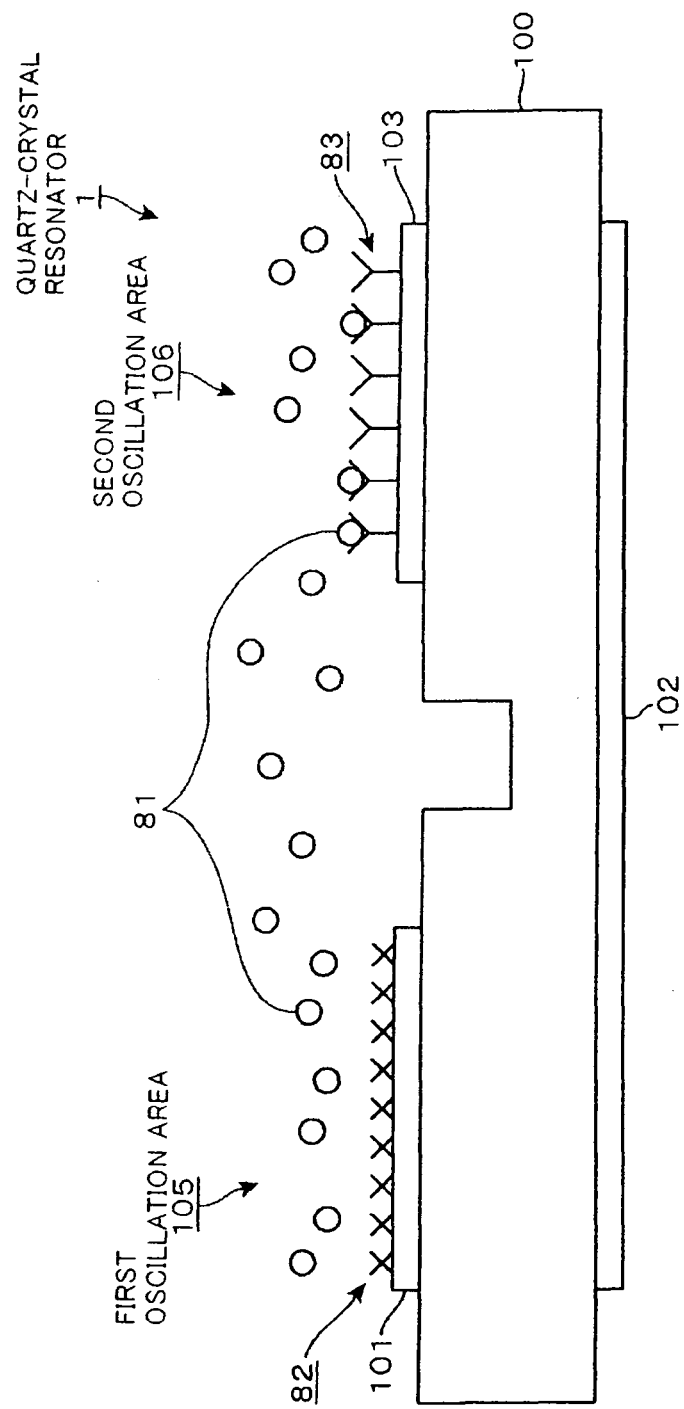
FIG. 4 is an explanatory view showing a mechanism for sensing an antigen in the quartz-crystal resonator.

On the front surface of the excitation electrode provided on one-side area of the quartz-crystal resonator 1, for example, on the front surface of the excitation electrode 101 on the first oscillation area 105, a block layer 82 made of an antibody (protein) not reacting with a substance to be sensed 81 contained in the sample solution is formed as shown on the left in FIG. 4, for instance. The block layer 82 plays a role of preventing the front surface of the excitation electrode 101 from adsorbing the substance to be sensed 81. Here, in order to reduce the adsorption of the substance to be sensed 81 by the excitation electrode 101, the excitation electrode 101 may be exposed instead of being covered. However, in a case where an antigen in blood or serum is the substance to be sensed 81 as in this embodiment, in order to prevent the excitation electrode 101 from adsorbing some component in blood, some kind of protein not allowing the adsorption of the component is preferably provided as the block layer 82.

On the other hand, on the excitation electrode provided on the other area of the quartz-crystal resonator 1, for example, on the excitation electrode 103 on the second oscillation area 106, an adsorption layer 83 made of an antibody selectively reacting and bonded with the substance to be sensed 81 being the antigen is provided as shown on the right in FIG. 4, for instance. The adsorption layer 83 plays a role of fixing the adsorption layer 83 in the sample solution onto the excitation electrode 103 by an antigen-antibody reaction.

The quartz-crystal resonator 1 having the above-described structure is set in a main body of the quartz-crystal sensor 3 shown in FIG. 2 in a predetermined direction, so that the excitation electrodes 101, 103 provided on the front surfaces of the oscillation areas 105, 106 are connected via the terminals 113, 114 to connection lines 116, 117 extending on the printed circuit board 301 being the holder provided in the main body of the quartz-crystal sensor 3. Further, the excitation electrode 102 on the rear surface side is connected via the terminal 115 to a ground line 118 extending on the printed circuit board 301.

Figure 5:
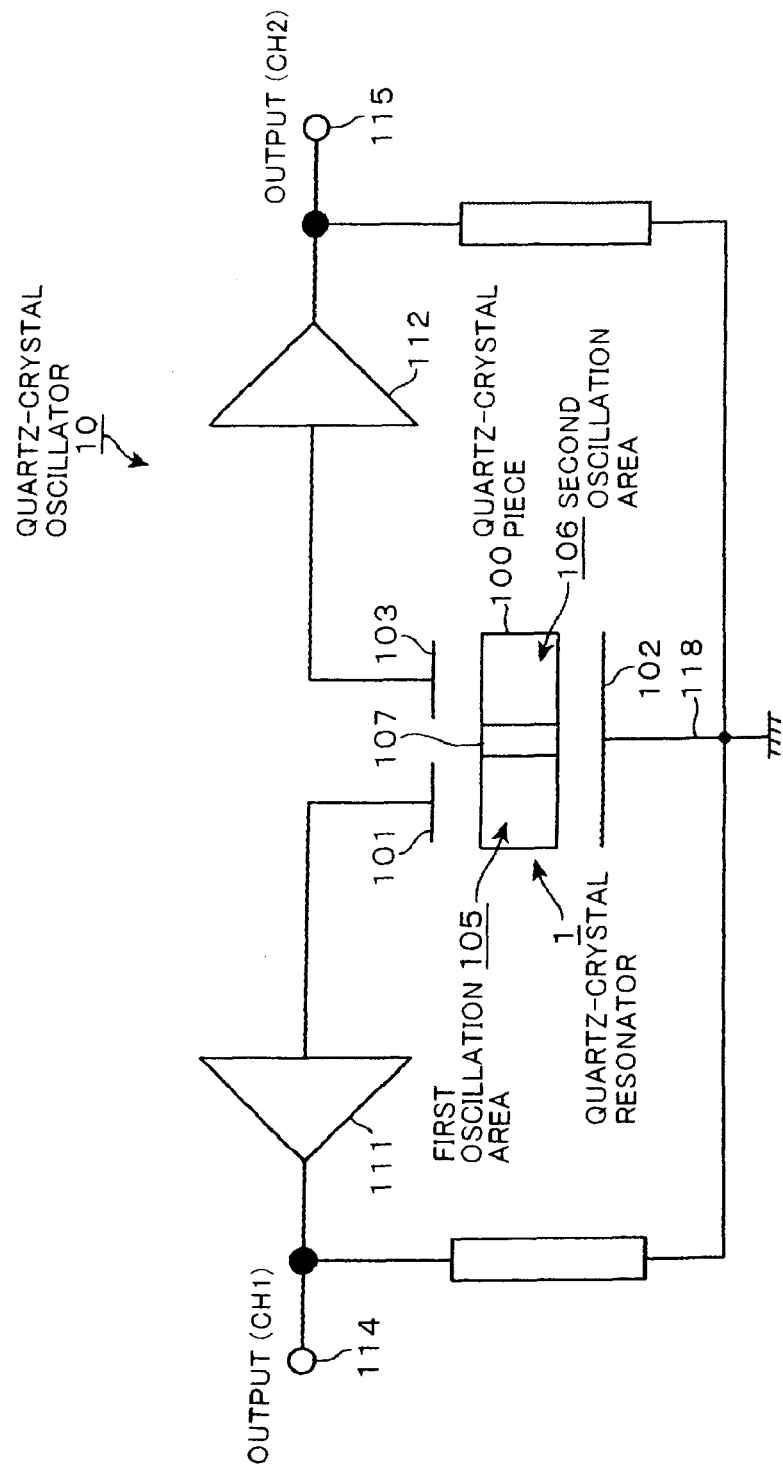
FIG. 5 is a schematic block diagram of a quartz-crystal oscillator circuit in which the quartz-crystal sensor is assembled.

As shown in FIG. 1, the quartz-crystal sensor 3 having the quartz-crystal resonator 1 set therein is connected to a casing 41 of the oscillator circuit unit 40, so that a quartz-crystal oscillator 10 including the quartz-crystal resonator 1 shown in FIG. 5 is formed. Its structure is described in Background Art and therefore a description thereof will be omitted. For example, when the quartz-crystal oscillator 10 is oscillated under a predetermined reference temperature atmosphere and in a state where the sample solution not containing the substance to be sensed 81 is supplied to the quartz-crystal sensor 3, that is, in a state where the substance to be sensed 81 is adsorbed by neither of the block layer 82 and the adsorption layer 83, a frequency signal having a first oscillation frequency "F0" is taken out from the first oscillation area 105 to be output from a channel 1, and a frequency signal having a second oscillation frequency "F1" is taken out from the second oscillation area 106 to be output from a channel 2.

On the other hand, when the sample solution contains the substance to be sensed 81, a mass load effect appearing as a result of the bonding of the substance to be sensed 81 with the adsorption layer 83 lowers a value of the second oscillation frequency "F1", and therefore, an amount of the substance to be sensed 81 in the sample solution can be calculated based on a variation in this oscillation frequency.

Here, in obtaining the variation in the oscillation frequency ascribable to the adsorption of the substance to be sensed 81, processing to find the variation in the oscillation frequency from a difference between the first oscillation frequency and the second oscillation frequency is performed in order to cancel the influence of an ambient temperature change.

At this time, when the frequency difference between the first oscillation frequency and the second oscillation frequency is too large, frequency-temperature characteristics of the oscillation frequencies from the respective channels become different, and even if the difference between the oscillation frequencies of the both channels is taken, the sufficient cancellation of the influence of the temperature change is not possible, as is described in Background Art. The present inventor has also found out that, when on the contrary the frequency difference is too small, it is not possible to accurately take out a variation in the oscillation frequency caused by the adsorption of the substance to be sensed 81 because the both oscillation frequencies interfere with each other due to the elastic coupling of the first oscillation area 105 and the second oscillation area 106.

Regarding these problems, by variously changing the oscillation frequencies of the frequency signals taken out from the areas 105, 106 of the quartz-crystal resonator 1, the present inventors have found out a condition capable of reducing the influence of the above-described problems to a negligible degree. Specifically, it has been found out that, when the frequency difference between the first and second oscillation frequencies, which are taken out from the first and second oscillation areas 105, 106 under the predetermined reference temperature atmosphere and in the state where the substance to be sensed 81 is not adsorbed by the first oscillation area 105 side, falls within a range of preferably not less than 0.2% nor greater than 2.2% of the first and second oscillation frequencies, more preferably not less than 0.5% nor greater than 1.1%, the frequency-temperature characteristics of the two areas 105, 106 become substantially the same and the elastic coupling of these areas 105, 106 is also effectively reduced.

For example, the present applicant has developed a quartz-crystal oscillator 10 in which a reference temperature atmosphere is, for example, 25° C. and oscillation frequencies from oscillation areas 105, 106 are about 9.1 MHz, and in this case, it has been confirmed that, when a difference between the first and second frequencies falls within a range of preferably not less than 20 kHz nor greater than 200 kHz, more preferably, not less than 50 kHz nor greater than 100 kHz, for example, is 50 kHz, the influence of the aforesaid problems is effectively reduced and highly reliable measurement results can be obtained. Therefore, in the quartz-crystal resonator 1 according to this embodiment, the first and second oscillation frequencies are adjusted in such a manner that the excitation electrodes 101, 103 different in, for example, thickness, that is, the excitation electrodes 101, 103 different in mass are formed on the oscillation areas 105, 106 respectively as shown in a vertical sectional view in FIG. 6 to change a mass load effect. For example, in this example, the excitation electrode 101 on the first oscillation area 105 is made thicker to make the first oscillation frequency F0 lower, while the excitation electrode 103 on the second oscillation area 106 is made thinner to make the second oscillation frequency F1 higher, whereby the difference between the oscillation frequencies taken out from the areas 105, 106 is adjusted to 50 kHz.

An example of a method of forming the excitation electrodes 101, 103 different in thickness is that an Au film having a thickness corresponding to the thickness of, for example, the excitation electrode 103 is formed by sputtering or the like on a front surface of a quartz-crystal substrate from which the quartz-crystal piece 100 is to be cut out, the Au film is coated with a resist, and portions, of the Au film, corresponding to contours of the excitation electrodes 101, 103 are exposed by photolithography. Next, by the removal of the exposed portions of the Au film by, for example, a KI solution, quartz crystal in these portions is exposed, whereby the excitation electrodes 101, 103 are formed, and thereafter, the excitation electrode 103 on the second oscillation area 106, for instance, is covered by a resist, while the front surface of the excitation electrode 101 on the first oscillation area 105 is kept exposed. In this state, the quartz-crystal substrate is immersed in the KI solution for a predetermined time and part of the excitation electrode 101 is etched off, whereby the excitation electrodes 101, 103 different in thickness can be formed. The excitation electrode 102 in the shape shown in FIG. 3(*b*) on the rear surface side is formed by sputtering, photolithography, and etching with, for example, a KI solution, and the shapes of the quartz-crystal piece 100 and the elastic boundary layer 17 can be formed by the combination of photolithography and etching with, for example, hydrofluoric acid.

By thus forming the excitation electrodes 101, 103 different in mass on the oscillation areas 105, 106, it is possible to oscillate a frequency signal including the second oscillation frequency, for example, "9.176 MHz" from the second oscillation area 106 to output this signal from the channel 2 under the reference temperature atmosphere of, for example, 25° C. and in the state where the substance to be sensed 81 is not adsorbed. Similarly, from the first oscillation area 105, it is possible to output a frequency signal including the first oscillation frequency, for example, "9.126 MHz" from the channel 1. Here, since the mass load effect lowers the oscillation frequency of the oscillation area 105 or 106 on which the excitation electrode 101 or 103 with a large mass is provided, in the quartz-crystal resonator 1, the excitation electrode 101 of the first oscillation area 105 is made thicker, contrary to the example shown in FIG. 6.

Figure 7:
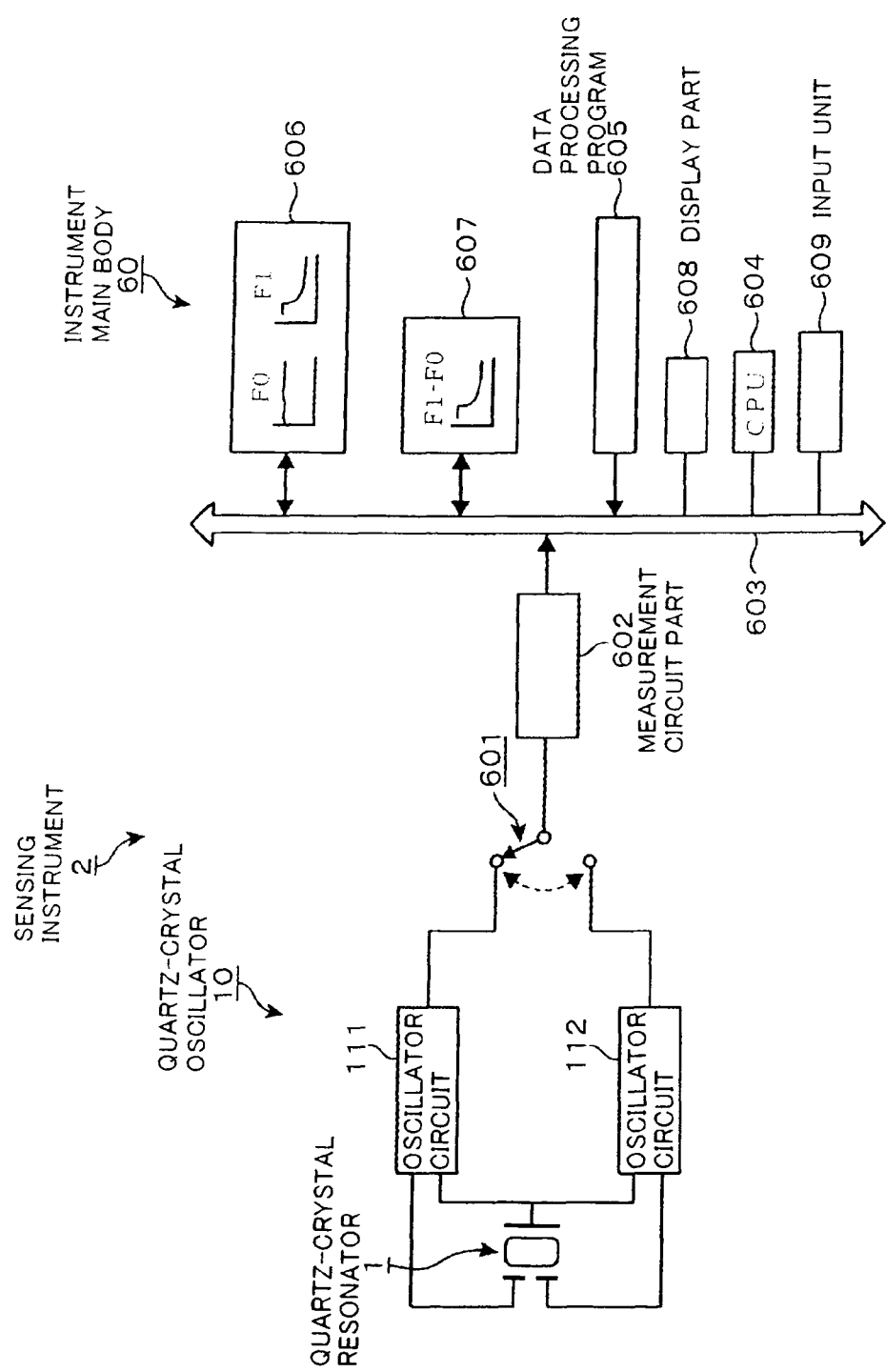
FIG. 7 is a block diagram showing the structure of the sensing instrument.

FIG. 7 is a block diagram of the sensing instrument 2. As described above, the quartz-crystal resonator 1 in the quartz-crystal sensor 3 and oscillator circuits 111, 112 in the oscillator circuit unit 40 form the quartz-crystal oscillator 10, and the quartz-crystal resonator 1 is connected to the instrument main body 60 via the oscillator circuits 111, 112. A measurement circuit part 602 is provided in a connection part between the quartz-crystal oscillator 10 and the instrument main body 60, and the measurement circuit part 602 plays a role of digitally processing, for example, the frequency signals being input signals to measure the oscillation frequencies of the respective channels. Further, on a preceding stage of the measurement circuit part 60, a switch part 601 fetching the output signals from the channels to the measurement circuit part 602 in sequence is provided, and the switch part 601 plays a role of fetching the frequency signals from the two oscillator circuits 111, 112 in a time-division manner so that the oscillation frequencies of the respective channels can be found in parallel. For example, one second is n-divided (n is an even number) and the oscillation frequencies of the respective channels are sequentially found by every 1/n-second processing, so that the frequency acquisition takes place at least once or more in one second though the frequencies are not completely simultaneously measured in a strict sense, and therefore, it is possible to obtain the frequencies of the respective channels practically simultaneously.

The instrument main body 60 is structured such that a CPU (central processing unit) 604, a storage unit storing data processing program 605, a first memory 606, a second memory 607, and the aforesaid measurement circuit part 602 are connected to one another via a data bus 603. Further, the aforesaid display part 608 such as a monitor and an input unit 609 such as a keyboard are connected to the data bus 603, and the instrument main body 60 is connected to a personal computer or the like, which is not shown in FIG. 7.

The data processing program 605 plays a role of obtaining time-series data relating to the oscillation frequencies of the respective channels based on signals output from the measurement circuit part 602 to store the obtained time-series data in the first memory 606. Further, in addition to this data obtaining operation, the data processing program 605 also has a function of calculating the difference "F1–F0" between time-series data in the same time zone relating to the oscillation frequency "F0" obtained from the channel 1 and the oscillation frequency "F1" obtained from the channel 2 to obtain time-series data of the difference data and storing the time-series data of the difference data in the second memory 607. Further, it is also structured to be capable of displaying these data on the display part 608 in response to a user's selection. The CPU 604, the data processing program 605, and the memories 606, 607 realizing these functions form a unit measuring the oscillation frequencies.

Next the operation of the sensing instrument 2 having the above-described structure will be described, taking, as an example, a method of finding the concentration of a certain kind of antigen in blood or serum. First, when the instrument main body 60 is activated and the quartz-crystal sensor 3 is inserted in an insertion port of the oscillator circuit unit 40, the oscillator circuits 111, 112 start their oscillations. The frequency signals output from the respective channels are sequentially fetched via the switch part 601 to the measurement circuit part 602, which A/D converts the frequency signals and applies signal processing to the resultant digital values, so that the oscillation frequencies "F0, F1" in a vapor atmosphere are taken out from the frequency signals of the two channels, and the operation for storing these oscillation frequencies in the first memory 606 substantially simultaneously (for example, at a ½ second time interval) is continued.

Next, when a user injects, for example, a solution of salt as a diluting liquid to the quartz-crystal sensor 3, the atmosphere of the quartz-crystal resonator 1 changes from the vapor phase to a liquid phase, so that the frequencies of the respective channels lower. Meanwhile, a sample solution in which serum collected from a human body is diluted, for example, ten times, with a diluting liquid such as, for example, a solution of salt is prepared, and when the sample solution is injected to the quartz-crystal sensor 3, the antigen-antibody reaction progresses on the excitation electrode 103 of the second oscillation area 106 on which the adsorption layer 83 is formed and a value of the frequency "F1" further lowers due to the mass load effect. When a temperature of the sample solution changes during this period, the value of the frequency "F1" increases or decreases according to the temperature change. On the other hand, from the channel 1 of the first oscillation area 105 side, the frequency "F0" changing according to the temperature of the sample solution but not dependent on the concentration of the substance to be sensed 81 is output.

The time-series data of the frequencies thus output from the respective channels are stored in the first memory 606, and in addition, the difference between the frequency "F1" of the channel 2 and the frequency "F0" of the channel 1 is calculated and the time-series data of the difference are stored in the second memory 607. The difference frequency may be found at some timing in the period in which the frequencies of the channels are sequentially fetched, and an example of the method for this may be such that the frequency "F0" of the channel 1 is fetched and then the frequency "F1" of the channel 2 is fetched, thereafter, "F0" is subtracted from "F1", and the difference therebetween is written to the second memory 607, or after the time-series data of the frequencies of the respective channels are obtained, time axes of these data are aligned and the time-series data of the difference are created.

In executing a series of these data processing, the frequency difference between the oscillation frequencies taken out from the first oscillation area 105 and the second oscillation area 106 under the 25° C. reference temperature atmosphere and in the state where the substance to be sensed 81 is not adsorbed by the first oscillation area 105 side is adjusted to, for example, 50 kHz which is a value equal to or more than 20 kHz, preferably equal to or more than 50 kHz, so that the elastic coupling of the two areas 105, 106 is reduced and an accurate variation in the oscillation frequency due to the adsorption of the substance to be sensed 81 is taken out as shown in later-described experiment results.

Subsequently, when, for example, the user selects a command for displaying the difference data between the channels by using the input unit 609, the selected difference data is displayed from the time-series data in the second memory 607 as a graph on the display part 608. Even when the frequencies "F0, F1" from the respective channels change in the course of a series of this operation due to a change in the ambient temperature, this temperature change occurs under the same condition on the common quartz-crystal resonator 1. Therefore, since the influence of the temperature change is canceled by taking the difference between these frequencies, the decrease in the frequency in the difference data stored in the second memory 607 can be said to be ascribable only to the adsorption of the antigen by the quartz-crystal resonator 1.

In this case as well, the frequency difference between the oscillation frequencies taken out from the first oscillation area 105 and the second oscillation area 106 under the 25° C. reference temperature atmosphere and in the state where the substance to be sensed 81 is not adsorbed by the first oscillation area 105 is adjusted to, for example, 50 kHz as described above, and the aforesaid frequency difference has a value not less than 20 kHz nor greater than 200 kHz, preferably not less than 50 kHz nor greater than 100 kHz, so that the frequency-temperature characteristics of the oscillation frequencies taken out from the respective areas 105, 106 are substantially the same even when the temperature of the sample solution changes. Therefore, by calculating the difference between these frequencies, it is possible to cancel the influence of the temperature change with high accuracy. Further, a variable factor that can be reduced by using the quartz-crystal oscillator 10 of the twin sensor type is not limited to the temperature change, but the present invention is also effective when, for example, vibration is applied from an external part and when the viscosity of the sample solution (blood or serum) changes.

Based on the variation in the difference data thus displayed, the user can find the concentration of the substance to be sensed 81 by using a relational expression (calibration curve) between the variation in the oscillation frequency and the concentration of the substance to be sensed 81, which expression is found in advance by the user. Here, the decision of the variation in the difference data and the decision of the concentration of the substance to be sensed 81 using the calibration curve may be automated in the sensing instrument 2 or the user may decide them by reading the data displayed on the display part 608, for instance.

The quartz-crystal resonator 1 of the twin sensor type according to this embodiment has the following effects. The difference between the oscillation frequencies of the two oscillation areas 105, 106 provided in the piezoelectric resonator 1 of the twin sensor type is a value falling within 0.2% to 2.2% of these oscillation frequencies; for example, the oscillation frequencies fall within a 4.0 MHz to 200 MHz range, for example, about 9.1 MHz (F0=9.126 MHz, F1=9.176 MHz), and the frequency difference falls within a 20 kHz to 100 kHz range, and is for example, 50 kHz. When the frequency difference falls within such a range, mutual interference between the oscillation frequencies due to the elastic coupling of the two oscillation areas 105, 106 is small, so that it is possible to accurately take out the oscillation frequencies of the respective areas 105, 106. Further, when the frequency difference falls within this range, since the frequency-temperature characteristics of the two areas 105, 106 are the same, it is possible to effectively cancel the influence of the frequency-temperature characteristics by taking the difference between these oscillation frequencies. As a result, for example, when the quartz-crystal resonator 1 is applied to the quartz-crystal sensor 3, highly reliable sensing results can be obtained.

Figure 6:
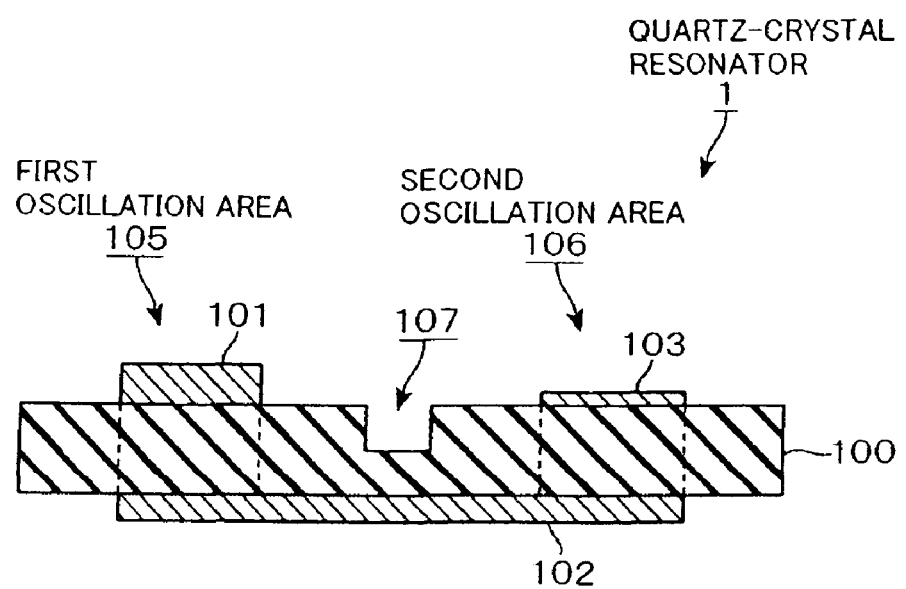
FIG. 6 is a vertical sectional view of the quartz-crystal resonator.
Figure 8:
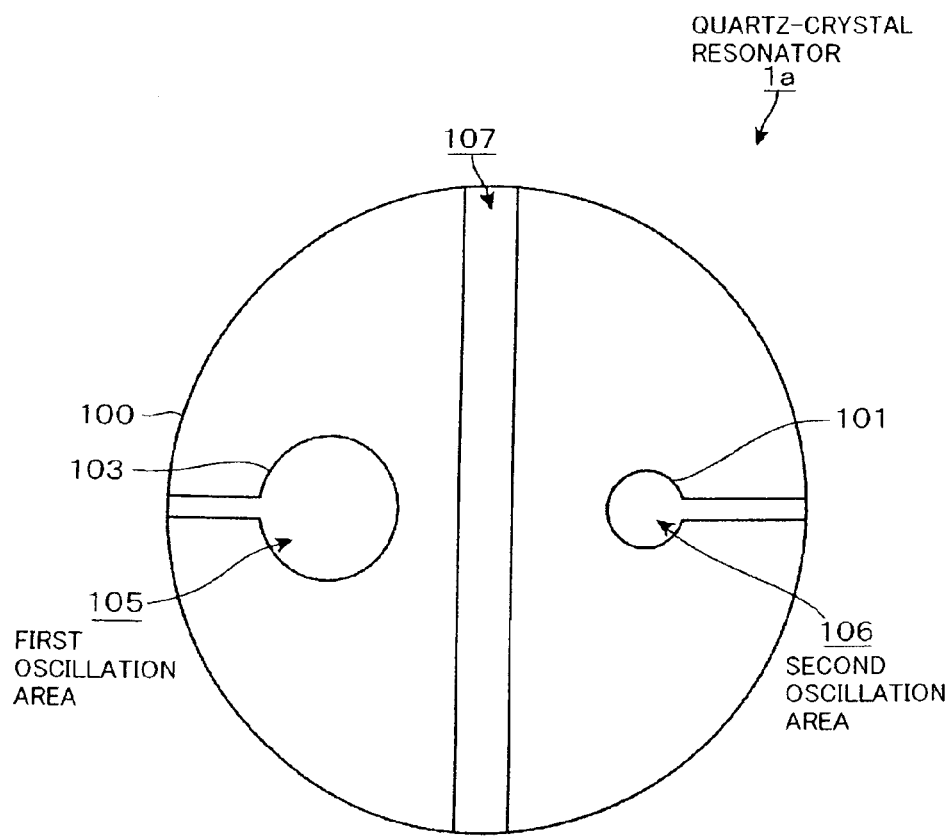
FIG. 8 is a plane view showing a modification example of the quartz-crystal resonator.
Figure 9:
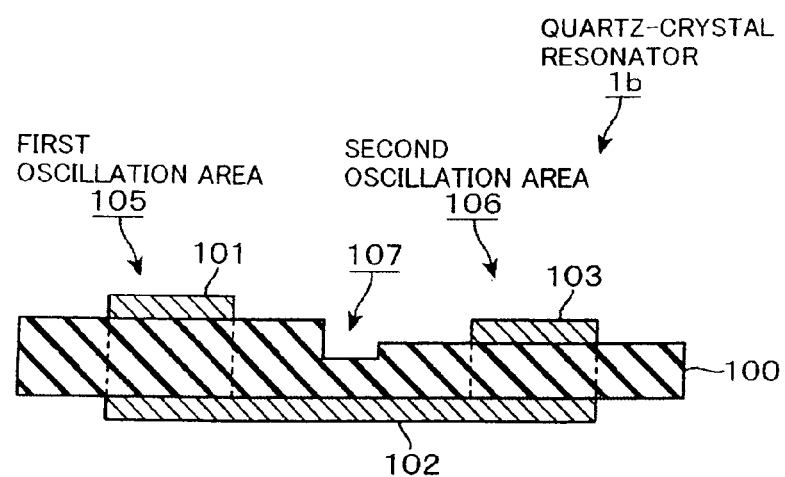
FIG. 9 is a vertical sectional view showing a second modification example of the quartz-crystal resonator.

Here, the method for adjusting the frequency difference between the oscillation frequencies taken out from the first oscillation area 105 and the second oscillation area 106 is not limited to the method of making the excitation electrodes 101, 103 formed on the front surface of the quartz-crystal piece 100 different in thickness, as shown in FIG. 6. Another example of the method of adjusting the oscillation frequencies may be such that excitation electrodes 101, 105 equal in thickness and different in area are formed on oscillation areas 105, 106 as in a quartz-crystal resonator 1a shown in FIG. 8. Another example of the method of adjusting the oscillation frequencies taken out from the respective areas 105, 106 may be such that a quartz-crystal piece 100 has different thicknesses in a first oscillation area 105 and in a second oscillation area 106 as in a quartz-crystal resonator 1b shown in FIG. 9.

Figure 10:
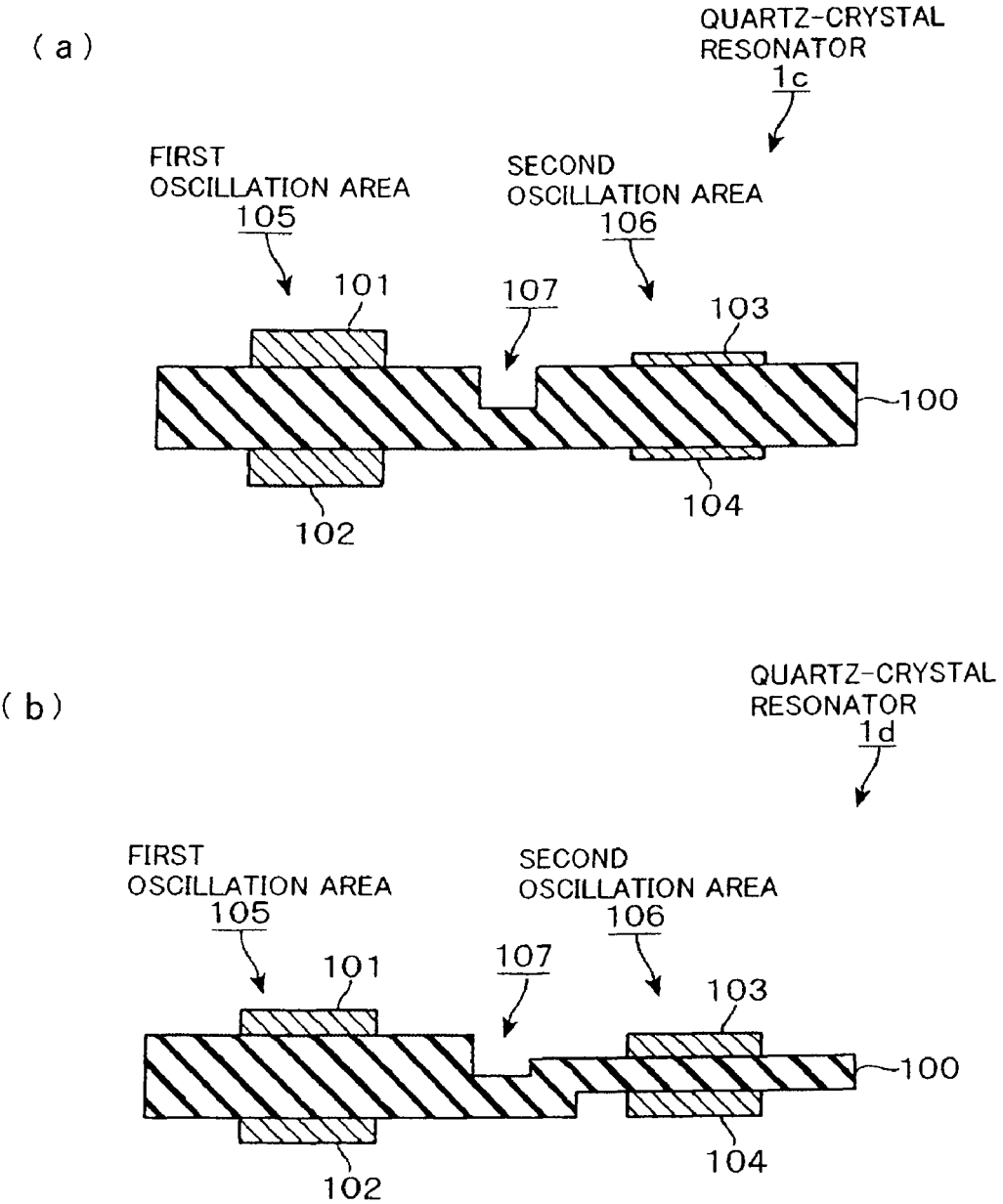
FIG. 10 are vertical sectional views showing a third and a fourth modification example of the quartz-crystal resonator.

These methods are not limited to the case where the thicknesses or sizes of the excitation electrodes 101, 103 or the thicknesses of the quartz-crystal piece 100 are adjusted from the front surface side of the quartz-crystal resonator 1, but an alternative method may be such that discrete excitation electrodes 101 to 104 are formed on front surfaces and rear surfaces of two oscillation areas and the excitation electrodes 101 to 104 on the front and rear surfaces are made different in thickness between the first oscillation area 105 and the second oscillation area 106, as in a quartz-crystal resonator 1c shown in FIG. 10(a), for instance. Another alternative structure, though not shown, may be such that excitation electrodes 101 to 104 formed on front and rear surfaces are made different in size similarly to the above-described case in FIG. 8, and still another alternative example is such that a quartz-crystal piece 100 is etched from front and rear surfaces so that the quartz-crystal piece 100 has different thicknesses in a first oscillation area 105 and a second oscillation area 106 as in a quartz-crystal resonator 1d shown in FIG. 10(b).

Further, the concave portion corresponding to the hole portion need not be provided in the printed circuit board 301 and the rubber sheet 302 forming the holder according to this embodiment. For example, the quartz-crystal sensor 3 may be structured such that the whole quartz-crystal resonator 1 is immersed, but in this case, the rear surface side on which the adsorption layer 83 is not provided is airtight space so as not to be in contact with the liquid.

Here, in forming the two oscillation areas 105, 106, the elastic boundary area need not be provided. However, when an AT-cut quartz-crystal piece is used whose thickness is adjusted so that the frequency of, for example, 9.126 MHz is oscillated and the oscillation areas 105, 106 are made to have different oscillation frequencies by the adjustment of, for example, the thickness of the excitation electrodes, it is preferable that the frequency difference is equal to or more than 10 kHz and less than 2 MHz, and further a separation distance between the oscillation areas 105, 106, that is, a distance d between the excitation electrodes 101, 103 is equal to or more than 0.1 mm and less than 2 mm as shown in FIGS. 11(a), (b). The reason is as follows.

Figure 12:
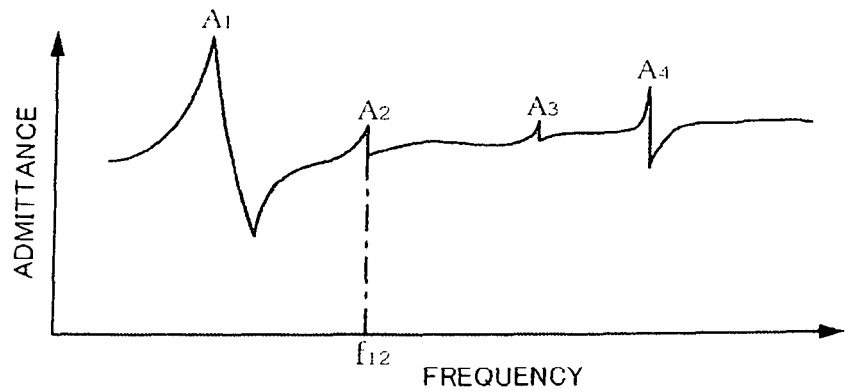
FIG. 12 are characteristic charts showing admittance characteristics of the two oscillation areas.
Figure 12:
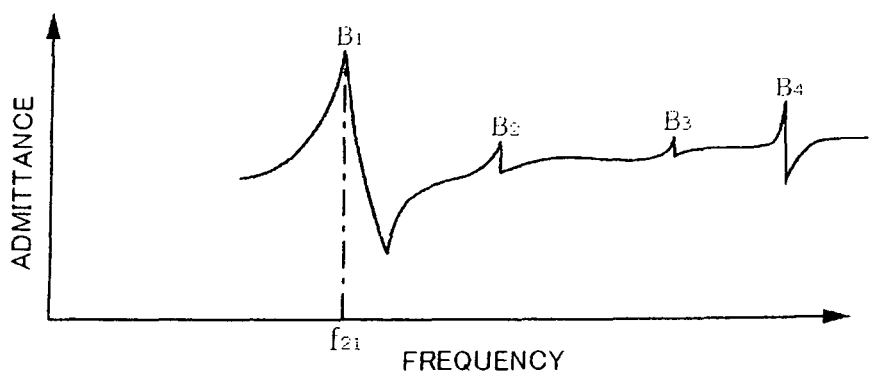

FIGS. 12(a), (b) show an admittance characteristic of the oscillation area 105 and an admittance characteristic of the oscillation area 106 respectively, and a frequency $f_{12}$ of secondary oscillation of the oscillation area 105 due to harmonics and a frequency $f_{21}$ of primary oscillation of the other oscillation area 106 sometimes approach each other. In this case, a frequency jump might occur due to the coupling of the primary oscillation and the secondary oscillation. The occurrence of the frequency jump makes a measurement value of the frequency unstable when a quartz-crystal resonator is used as a sensing sensor, which hinders the accurate measurement. Note that A1, B1 in FIG. 12 represent characterizing portions corresponding to the primary oscillation, and A2 to A4 and B2 to B4 represent characterizing portions corresponding to the secondary oscillation.

Figure 13:
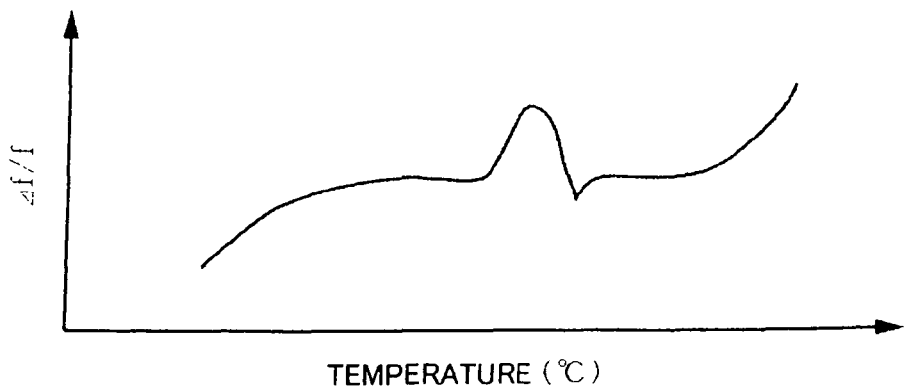
FIG. 13 is a characteristic chart showing a frequency-temperature characteristic of the quartz-crystal resonator.
Figure 14:
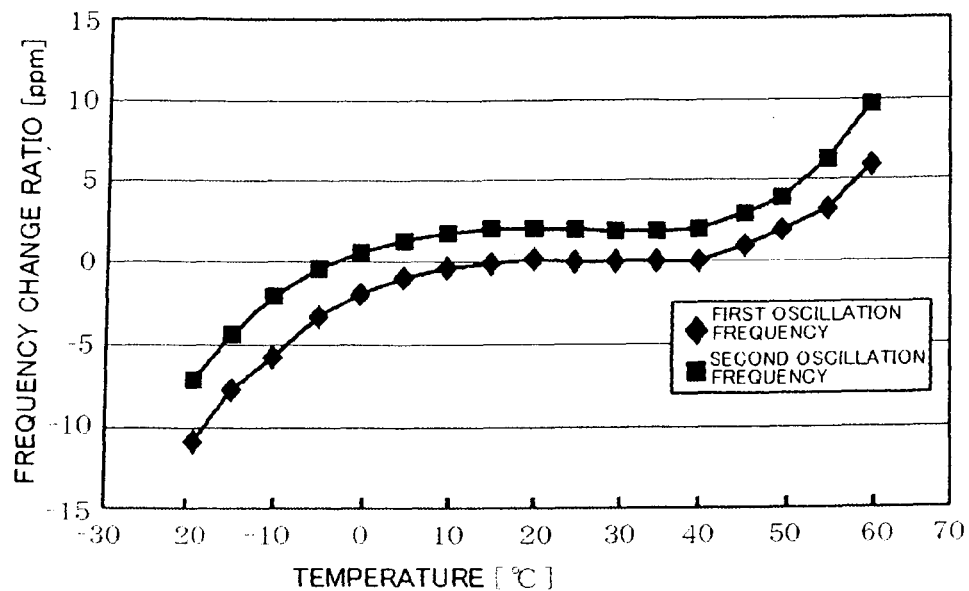
FIG. 14 is a characteristic chart showing temperature characteristics of frequency change ratios of a quartz-crystal resonator according to a comparative example.

FIG. 13 shows a frequency-temperature characteristic of one of the oscillation areas 105, 106, and is a chart showing the state where the frequency jump is occurring. A temperature at which the frequency jump is occurring is in a room temperature range. Therefore, in order to prevent the occurrence of the frequency jump due to the approach between the frequency of the primary oscillation of one of the oscillation areas and the frequency of the secondary oscillation of the other, the frequency difference is preferably 10 kHz or more, more preferably, 20 kHz or more as described in the above embodiment. Further, when the frequency difference becomes 2 MHz or more, the frequency-temperature characteristics of the oscillation areas 105, 106 become different, and therefore, the design in which the frequency difference exceeds 2 MHz should be avoided, and desirably the frequency is, for example, 100 kHz or less as described in the above embodiment.

Furthermore, setting the distance d between the excitation electrodes 101, 103 to 0.1 mm or less causes the generation of stray capacitance between the excitation electrodes 101, 103 and setting the distance d to 2.0 mm or more results in a large separation distance between the excitation electrodes 101, 103, and therefore, the both are not advisable in view of increasing a matching degree of the both temperature characteristics. Therefore, the distance d is preferably equal to or more than 0.1 mm and less than 2 mm.

EXAMPLES

Experiment 1

A quartz-crystal resonator 1 of a twin sensor type was fabricated, a frequency difference between oscillation frequencies taken out from a first oscillation area 105 and a second oscillation area 106 was varied, and their temperature characteristics were compared.

A. Experiment Condition

Figure 3:
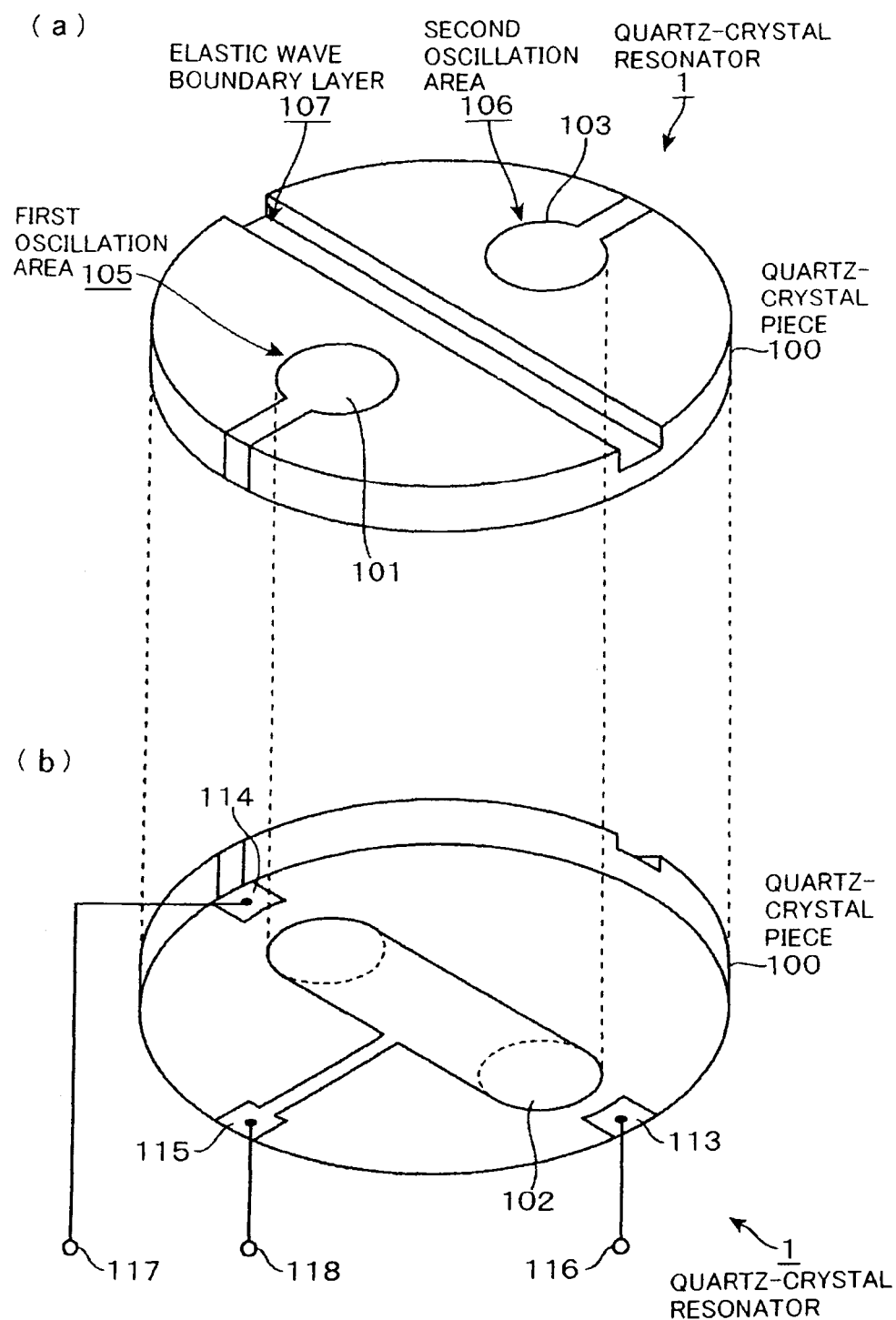
FIG. 3 are perspective views showing an external appearance of a quartz-crystal resonator assembled in the quartz-crystal sensor.

As a method of adjusting the frequency difference, the method described by using FIG. 3 and FIG. 6 was employed, that is, excitation electrodes 101, 103 formed on a front surface of a quartz-crystal piece 100 were made different in thickness. Concretely, with the thickness of the excitation electrode 103 of the second oscillation area 106 being fixed, the adjustment was made in such a manner that the thickness of the excitation electrode 101 of the first oscillation area 105 was made larger than that of the excitation electrode 103 to make the frequency difference large, and was set close to the thickness in the second oscillation area 106 side to make the frequency difference small. The two excitation electrodes 101, 103 were equal in area, and the thickness of the quartz-crystal piece 100 and the thickness of an excitation electrode 102 on a rear surface side were set equal between the two areas 105, 106. The excitation electrodes 101 to 103 were connected to the Colpitts oscillator circuits 111, 112 shown in FIG. 5, and frequency characteristics of frequency signals output from respective channels were examined, with a temperature of an environment where a quartz-crystal sensor 3 was placed being varied in a $-°20$ C. to 60° C. range while the quartz-crystal sensor 3 was filled with a solution of salt being a buffer solution.

Example 1

Frequency-temperature characteristics of a quartz-crystal resonator 1 whose oscillation frequencies at a reference temperature of 25[° C.] were set as follows were examined.
first oscillation frequency F0: 9.126 [MHz]
second oscillation frequency F1: 9.176 [MHz]
frequency difference $\Delta F=|F1-F0|=50$ [kHz] (about 0.54% of the oscillation frequencies)

Comparative Example 1

Frequency-temperature characteristics of a quartz-crystal resonator 1 whose oscillation frequencies at a reference temperature of 25[° C.] were set as follows were examined.
first oscillation frequency F0: 9.176 [MHz]
second oscillation frequency F1: 9.176 [MHz]
frequency difference $\Delta F=|F1=F0|=0$ [kHz] (0% of the oscillation frequencies)

Comparative Example 2

Frequency-temperature characteristics of a quartz-crystal resonator 1 whose oscillation frequencies at a reference temperature of 25[° C.] were set as follows were examined.
first oscillation frequency F0: 9.161 [MHz]
second oscillation frequency F1: 9.176 [MHz]
frequency difference $\Delta F=|F1=F0|=15$ [kHz] (about 0.16% of the oscillation frequencies)

Comparative Example 3

Frequency-temperature characteristics of a quartz-crystal resonator 1 whose oscillation frequencies at a reference temperature of 25[° C.] were set as follows were examined.
first oscillation frequency F0: 8.926 [MHz]
second oscillation frequency F1: 9.176 [MHz]
frequency difference $\Delta F=|F1=F0|=250$ [kHz] (about 2.7% of the oscillation frequencies)

B. Experiment Results

The results of (example 1), (comparative example 1) to (comparative example 3) are shown in FIG. 14 to FIG. 17 respectively. In the drawings, the horizontal axis represents the temperature of the atmosphere where the quartz-crystal sensor 3 is placed and the vertical axis represents percentage ([ppm]) of an oscillation frequency variation when the ambient temperature is changed from the reference temperature of 25[° C.], relative to the oscillation frequencies at the reference temperature (hereinafter, referred to as a frequency change ratio). In each of the drawings, the frequency change ratio of the first oscillation frequency is plotted with rhombuses "♦" colored in black, and that of the second oscillation frequency is plotted with squares "■" colored in black. Here, in the graphs in FIG. 15 to FIG. 17, the frequency change ratio of the second oscillation frequency is plotted at positions higher by 2 ppm than actual data for convenience sake so that the frequency change ratios of the first and second oscillation frequencies do not overlap and thus a difficulty in discrimination between them is avoided.

Figure 11:
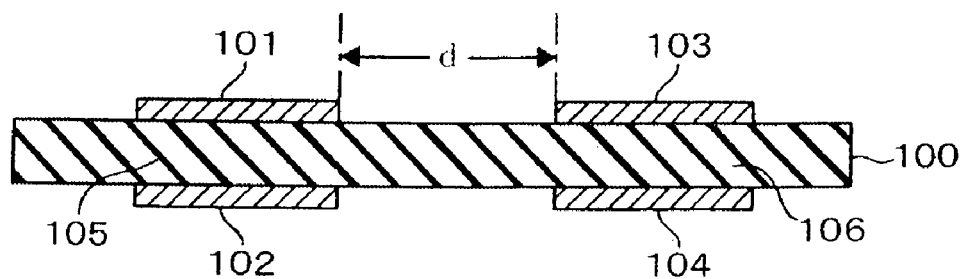
FIG. 11 are side views showing a separation distance between two oscillation areas in the quartz-crystal resonator.
Figure 11:
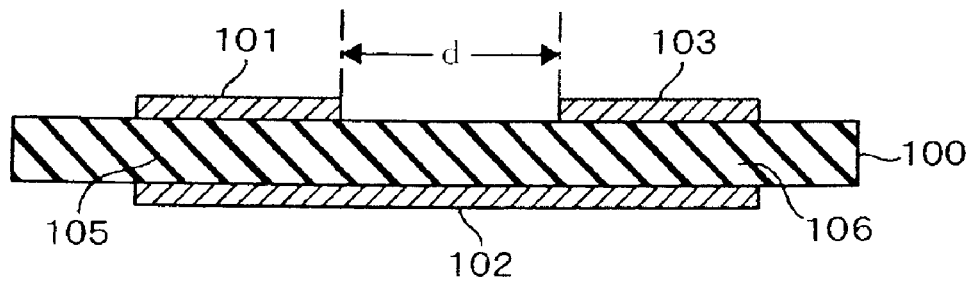

According to the result of (example 1) shown in FIG. 11, the frequency change ratios of the first oscillation frequency and the second oscillation frequency changed in accordance with the temperature change so as to depict substantially the same curve when the frequency difference $\Delta F$ between the first oscillation frequency and the second oscillation frequency was 50 [kHz]. This indicates that the first oscillation frequency and the second oscillation frequency exhibit substantially the same frequency-temperature characteristic in accordance with the change in the ambient temperature, and the frequency difference therebetween is a substantially fixed value not dependent on the temperature change. The present inventors conducted the similar additional experiment also when the second oscillation frequency F1 was fixed to 9.176 [MHz] (reference temperature 25[° C.]) and the frequency difference ΔF was changed to 20 (about 0.22% of the oscillation frequencies) and 100 (about 1.1% of the oscillation frequencies) [kHz], and confirmed that in these quartz-crystal resonators 1 as well, the frequency-temperature characteristics of the first and second oscillation frequencies were substantially the same, and by taking the frequency difference, it is possible to cancel the influence of the frequency-temperature characteristic, and thus they have high frequency stability.

Figure 15:
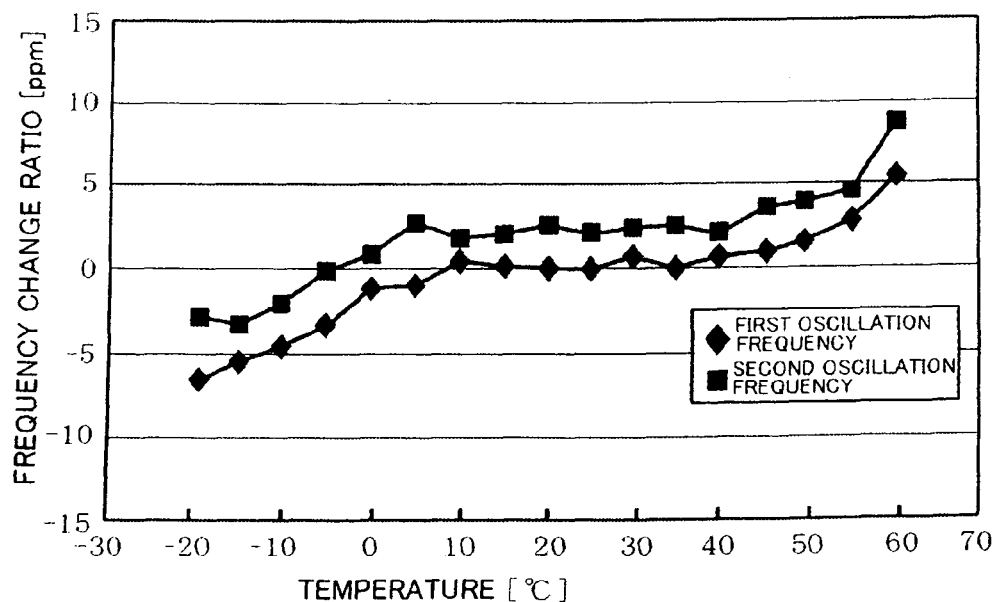
FIG. 15 is a characteristic chart showing temperature characteristics of frequency change ratios of a quartz-crystal resonator according to a comparative example.
Figure 16:
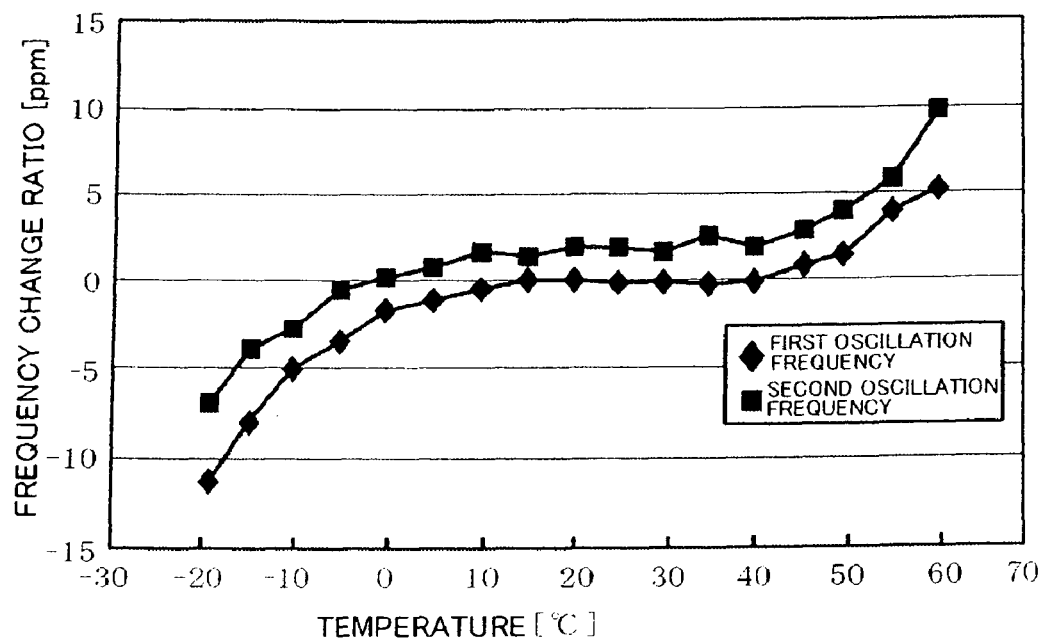
FIG. 16 is a second characteristic chart showing temperature characteristics of frequency change ratios of a quartz-crystal resonator according to a comparative example.

On the other hand, in (comparative example 1) in which the frequency difference ΔF was 0 [kHz], the oscillation frequencies exhibited unstable frequency change ratios in accordance with the temperature change and the frequency difference was not constant as shown in FIG. 15, and it was difficult to cancel the influence of the frequency-temperature characteristic even with the use of the quartz-crystal sensor 3 of the twin sensor type. A possible reason why the two oscillation frequencies present the unstably changing frequency-temperature characteristics is as follows. For example, when the oscillation frequencies are taken out while the first and second oscillation areas 105, 106 are oscillated independently, they present the same temperature characteristic, but when they are oscillated simultaneously, the first and second oscillation areas 105, 106 are elastically coupled to cause mutual interference. Further, as shown in FIG. 16, in (comparative example 2) in which the frequency difference ΔF was 15 [kHz], it is seen that the two temperature characteristics tend to present changes that gradually match each other, compared with (comparative example 1), but further matching of the temperature characteristics is practically required.

Figure 17:
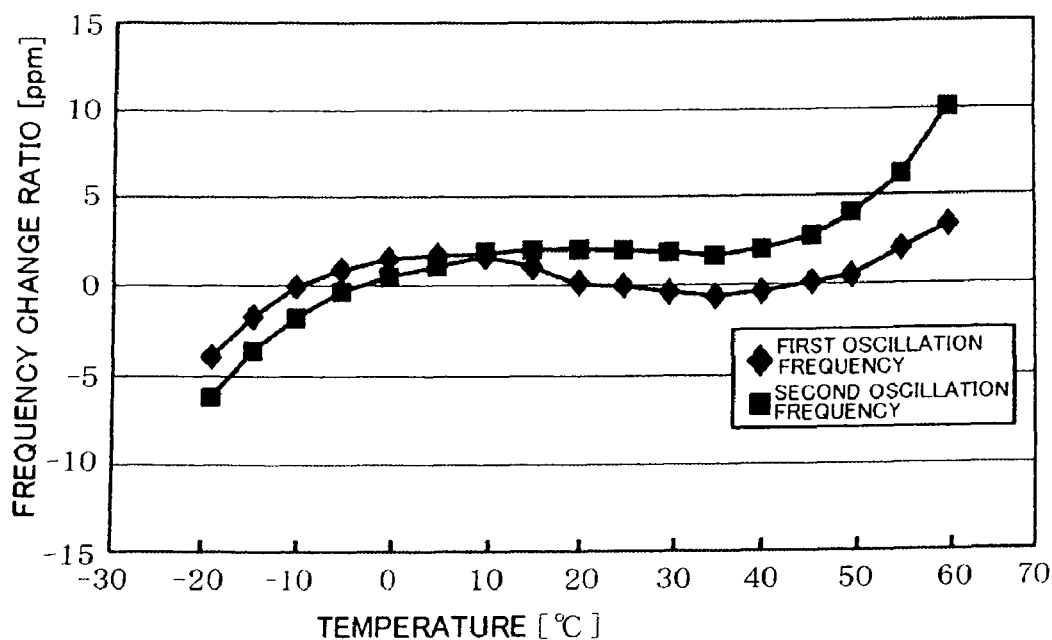
FIG. 17 is a third characteristic chart showing temperature characteristics of frequency change ratios of a quartz-crystal resonator according to a comparative example.
Figure 18:
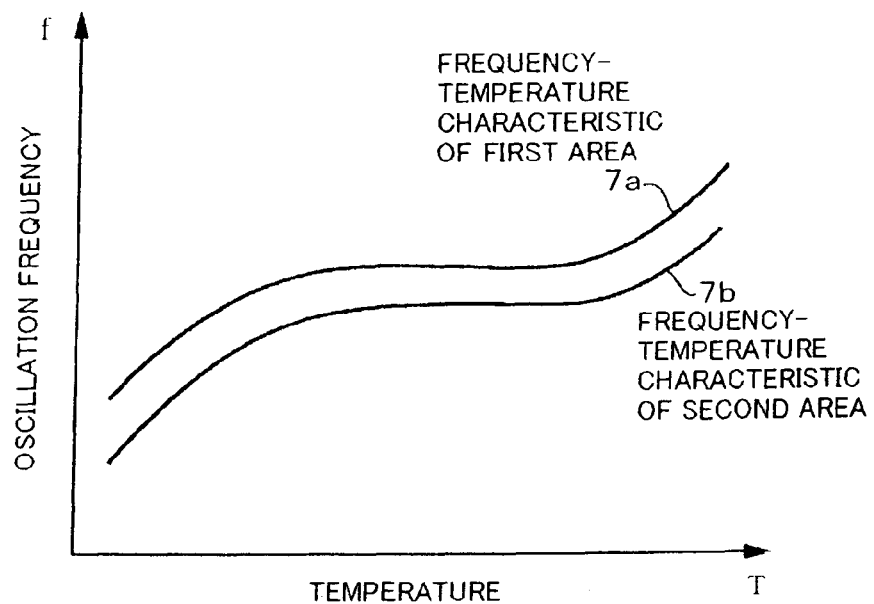
FIG. 18 is a characteristic chart showing frequency-temperature characteristics of a conventional quartz-crystal resonator of a twin sensor type.
Figure 19:
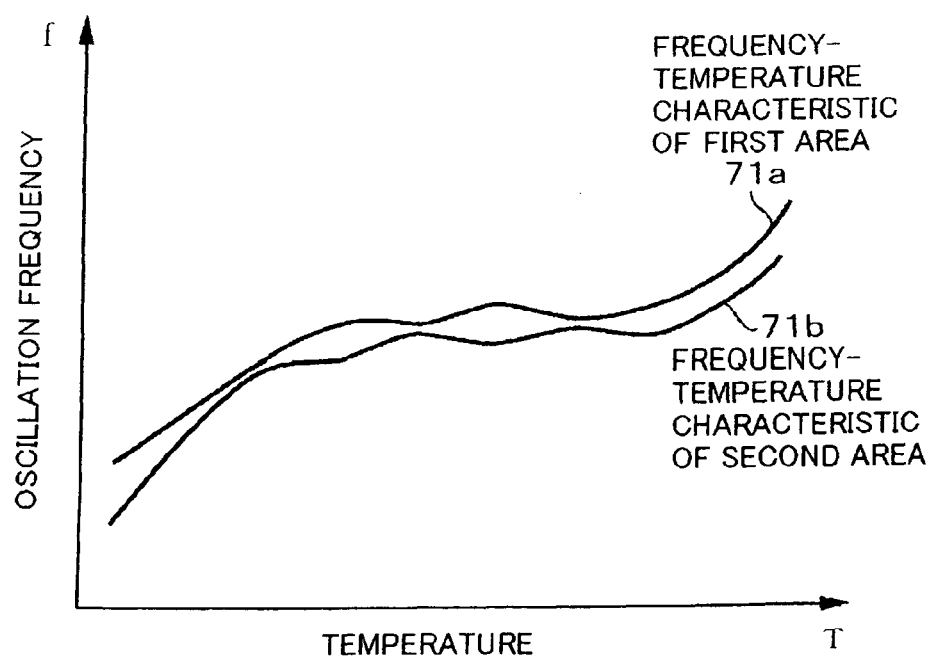
FIG. 19 is a second characteristic chart showing frequency-temperature characteristics of the conventional quartz-crystal resonator of the twin sensor type.
Figure 20:
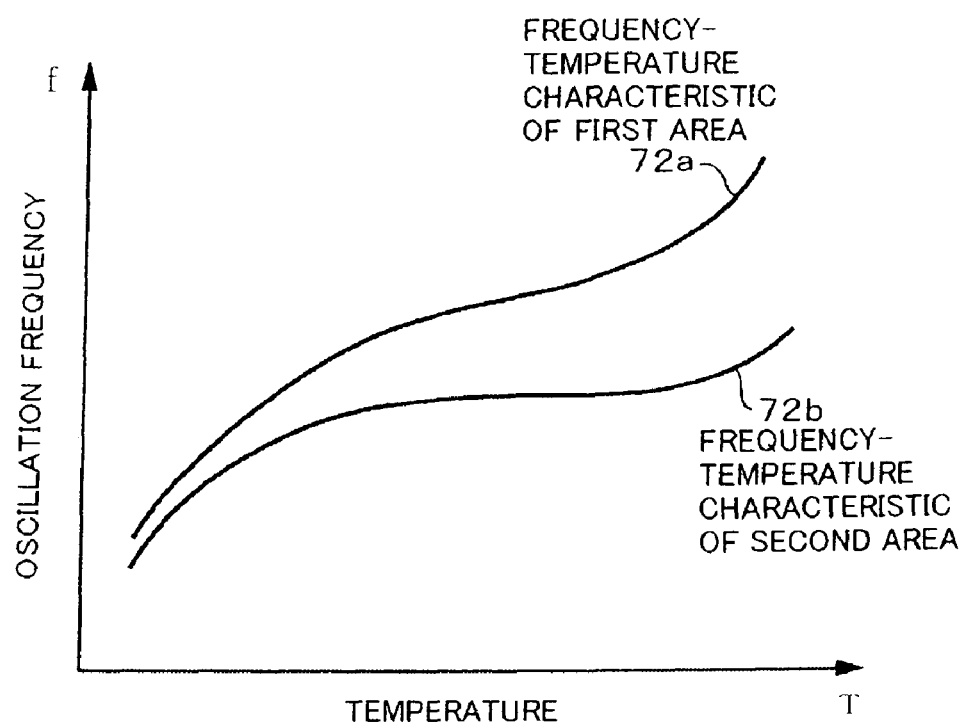
FIG. 20 is a third characteristic chart showing frequency-temperature characteristics of the conventional quartz-crystal resonator of the twin sensor type.

Further, as seen in the result of (comparative example 3) in which the frequency difference ΔF was 250 [kHz], the frequency change ratios of the first and second oscillation frequencies present changes depicting different curves in accordance with the temperature change as shown in FIG. 17, and in this case, the constant frequency difference cannot be obtained in accordance with the temperature change. Compared with (comparative examples 1, 2), in (comparative example 3), there is not seen a phenomenon that the frequency change ratios of the oscillation frequencies unstably change, and the frequency change ratios present changes depicting smooth curves. A possible reason for this is that, when the frequency difference between the two oscillation areas 105, 106 increases, the areas 105 present different frequency-temperature characteristics, and as a result, the frequency difference becomes not constant.

Furthermore, the present inventors conducted the same experiment with the second oscillation frequency F1 being fixed to 31.0 [MHz] (reference temperature 25[° C.]), and when the frequency difference ΔF was set to 70 (about 0.23% of the oscillation frequencies), 170 (about 0.55% of the oscillation frequencies), and 340 (about 1.1% of the oscillation frequencies) [kHz], the same temperature characteristics of the frequency change ratios as those shown in FIG. 11 (example 1) were confirmed. On the other hand, when the frequency difference ΔF was set to 0 (about 0% of the oscillation frequencies) and 50 (about 0.16% of the oscillation frequencies) [kHz], the same temperature characteristics as those in (comparative examples 1, 2) shown in FIG. 15 and FIG. 16 were confirmed, and when the frequency difference ΔF was set to 840 (about 2.7% of the oscillation frequencies) [kHz], the same temperature characteristics as those of (comparative example 3) shown in FIG. 17 were confirmed. From this, it has been confirmed that even when the oscillation frequencies are changed, it is possible to obtain a constant frequency difference irrespective of the temperature change, provided that the frequency difference falls within a 0.2% to 2.2% range of the oscillation frequencies.

The invention claimed is:

1. A sensing device, comprising:
a piezoelectric resonator comprising a first oscillation area which is provided in a piezoelectric piece made from an AT cut crystal for taking out a first oscillation frequency under a predetermined reference temperature atmosphere; a second oscillation area, which is provided in an area different from said first oscillation area, for taking out a second oscillation frequency different from the first oscillation frequency under the reference temperature atmosphere, wherein an elastic boundary area is provided in the piezeoelectric piece between said first oscillation area and said second oscillation area;
excitation electrodes provided on one surface side and another surface side of the piezoelectric piece in said first oscillation area and said second oscillation area;
a first oscillator circuit for taking out said first oscillation frequency from said first oscillation area;
a second oscillator circuit, different from said first oscillation circuit, for taking out said second oscillation frequency from said second oscillation area; and
a processing unit which calculates a difference between said second oscillation frequency and said first oscillation frequency and cancels out an oscillation variation component included in said second oscillation frequency corresponding to a change in temperature of said piezoelectric resonator;
wherein an adsorption layer that adsorbs a sensed substance is not formed on one of said excitation electrodes, said one electrode being in said first oscillation area;
wherein an adsorption layer that adsorbs the sensed substance is formed on another of the excitation electrodes, said another electrode being on said one surface side of said second oscillation area;
wherein a frequency difference between the first oscillation frequency and the second oscillation frequency, in said reference temperature atmosphere, is not less than 0.2% nor greater than 1.1% of the first and second oscillation frequencies; and
wherein the frequency difference is adjusted by making values of at least one of the following (i) and (ii) different between said first oscillation area and said second oscillation area:
(i) masses of said excitation electrodes provided on the one surface side and the other surface side across the piezoelectric piece in said first oscillation area and said second oscillation area; and
(ii) thickness of the piezoelectric piece in said first oscillation area and said second oscillation area.

2. The sensing device of claim 1, wherein in the first oscillation area and the second oscillation area, masses of the excitation electrodes and thickness of the piezoelectric piece are formed so that the oscillation frequencies of the first oscillation frequency and/or the second oscillation frequency are not less than 4.0 MHz nor greater than 200 MHz.

3. A sensing device, comprising:
a piezoelectric resonator comprising:
a piezoelectric piece made from an AT cut crystal and having a first surface side and a second surface side;

a first oscillation area which is provided in the piezoelectric piece for taking out a first oscillation frequency under a predetermined reference temperature atmosphere;

a second oscillation area, which is provided in the piezoelectric piece in an area different from said first oscillation area, for taking out a second oscillation frequency different from the first oscillation frequency under the reference temperature atmosphere; and an elastic boundary area which is provided in the piezoelectric piece between said first oscillation area and said second oscillation area;

the sensing device further comprising:

a first excitation electrode provided on said first surface side of the piezoelectric piece in said first oscillation area;

a second excitation electrode provided on said first surface side of the piezoelectric piece in said second oscillation area;

at least one third electrode formed on said second surface side of the piezoelectric piece;

a first oscillator circuit for taking out said first oscillation frequency from said first oscillation area;

a second oscillator circuit, different from said first oscillation circuit, for taking out said second oscillation frequency from said second oscillation area; and a processing unit which calculates a difference between said second oscillation frequency and said first oscillation frequency and cancels out an oscillation variation component included in said second oscillation frequency corresponding to a change in temperature of said piezoelectric resonator;

wherein an adsorption layer that adsorbs a sensed substance is not formed on said first excitation electrode;

wherein an adsorption layer that adsorbs the sensed substance is formed on said second excitation electrode;

wherein a frequency difference between the first oscillation frequency and the second oscillation frequency, in said reference temperature atmosphere, is not less than 0.2% nor greater than 1.1% of the first and second oscillation frequencies; and wherein the frequency difference is adjusted by making values of at least one of the following (i) and (ii) different between said first oscillation area and said second oscillation area:

(i) masses of said first excitation electrode and second excitation electrode; and (ii) thickness of the piezoelectric piece in said first oscillation area and said second oscillation area.

4. The sensing device of claim 3, wherein said frequency difference is adjusted by forming different masses and thicknesses of the first excitation electrode and second excitation electrode; and wherein mass and thickness of the first excitation electrode and second excitation electrode are formed so that the oscillation frequency of the first oscillation frequency and/or the second oscillation frequency are not less than 4.0 MHz nor greater than 200 MHz.

* * * * *